United States Patent
Lagaron Cabello et al.

(10) Patent No.: US 12,419,838 B2
(45) Date of Patent: *Sep. 23, 2025

(54) PHARMACEUTICAL FORMULATION WITH IMPROVED SOLUBILITY AND BIOAVAILABILITY

(71) Applicants: Consejo Superior de Investigaciones Cientificas (CSIC), Madrid (ES); BIOINICIA, S.L., Valencia (ES)

(72) Inventors: Jose Maria Lagaron Cabello, Valencia (ES); Cristina Prieto Lopez, Lugo (ES); Jose Manuel Valle Baz, Castellon de la Plana (ES); David Galan Nevado, Malaga (ES); Julia Hrakovsky, Gdynia (PL)

(73) Assignees: Consejo Superior de Investigaciones Cientificas (CSIC), Madrid (ES); BIOINICIA, S.L., Valencia (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/972,172

(22) Filed: Oct. 24, 2022

(65) Prior Publication Data
US 2023/0040719 A1 Feb. 9, 2023

Related U.S. Application Data

(62) Division of application No. 17/255,680, filed as application No. PCT/EP2019/067342 on Jun. 28, 2019, now abandoned.

(30) Foreign Application Priority Data

Jun. 29, 2018 (EP) .................................... 18382484

(51) Int. Cl.
*A61K 9/10* (2006.01)
*A61K 9/14* (2006.01)
(Continued)

(52) U.S. Cl.
CPC ............ *A61K 9/146* (2013.01); *A61K 9/1611* (2013.01); *A61K 9/1652* (2013.01);
(Continued)

(58) Field of Classification Search
CPC ...... A61K 45/06; A61K 9/146; A61K 9/1611; A61K 9/1652; A61K 9/1682; A61K 9/1694; B82Y 30/00; B82Y 40/00; B82Y 5/00
See application file for complete search history.

(56) References Cited

U.S. PATENT DOCUMENTS 5,049,322 A 9/1991 Devissaguet et al.
11,253,833 B2 * 2/2022 Lagaron Cabello ........................ A61K 9/5063

(Continued)

FOREIGN PATENT DOCUMENTS

| WO | 9713503 | 4/1997 |
| WO | 2015120861 A1 | 8/2015 |
| WO | 2016086193 A1 | 6/2016 |

OTHER PUBLICATIONS

Prieto et al. (Mol. Pharmaceutics 2021, 18, 2947-2958) (Year: 2021).*

(Continued)

*Primary Examiner* — Ernst V Arnold
(74) *Attorney, Agent, or Firm* — Seed Intellectual Property Law Group LLP

(57) ABSTRACT

The present invention relates to a pharmaceutical formulation comprising at least one active pharmaceutical ingredient (API) having low aqueous solubility or a pharmaceutically acceptable salt thereof in the form of particles of a size between 1 and 800 nm, wherein said particles are encapsulated within a large microparticle of a size between 1 and 100 μm formed by a matrix comprising at least an excipient. Therefore, the API is entrapped or encapsulated in the (Continued)

microparticles of excipients. This pharmaceutical formulation contains the pharmaceutical active ingredient having improved solubility and subsequently supra-bioavailability.

3 Claims, 7 Drawing Sheets

(51) Int. Cl.
  A61K 9/16    (2006.01)
  A61K 9/50    (2006.01)
  A61K 45/06   (2006.01)
  B82Y 5/00    (2011.01)
  B82Y 30/00   (2011.01)
  B82Y 40/00   (2011.01)
(52) U.S. Cl.
  CPC ............ A61K 9/1694 (2013.01); A61K 45/06 (2013.01); B82Y 5/00 (2013.01); B82Y 30/00 (2013.01); B82Y 40/00 (2013.01)

(56) References Cited

U.S. PATENT DOCUMENTS

2004/0071781 A1    4/2004    Chattopadhyay et al.
2005/0008704 A1    1/2005    Ray et al.

OTHER PUBLICATIONS

Bohr et al., "Release profile and characteristics of electrosprayed particles for oral delivery of a practically insoluble drug", Journal of The Royal Society, Interface, 2012, vol. 9, pp. 2437-2449, 13 pages.
Bohr et al., "Application of Spray-drying and Electrospraying/Electospinning for Poorly Watersoluble Drugs: A Particle Engineering Approach", Current Pharmaceutical Design, 2014, vol. 20, pp. 325-348, 24 pages.
Valo et al., "Electrospray encapsulation of hydrophilic and hydrophobic drugs in poly(L-lactic acid) nanoparticles", Small, 2009, vol. 5, Issue 15, pp. 1791-1798.
Kawakami, "Miscibility analysis of particulate solid dispersions prepared by electrospray deposition", ELSEVIER, ScienceDirect, International Journal of Pharmaceutics, 2012, vol. 433, Issues 1-2, pp. 71-78.
Margulis-Goshen & Magdassi, "Formation of simvastatin nanoparticles from microemulsion", ELSEVIER, Science Direct, Nanomedicine: Nanotechnology, Biology and Medicine, 2009, vol. 5, Issue 3, pp. 274-281.
Torchilin, "Multifunctional nanocarriers", ELSEVIER, ScienceDirect, Advanced Drug Delivery Reviews, 2012, vol. 64, Supplement, pp. 302-315.
Jyothi et al., "Microencapsulation techniques, factors influencing encapsulation efficiency", Journal of Microencapsulation, 2010, vol. 27, Issue 3, pp. 187-197.
Mora-Huertas et al., "Polymer-based nanocapsules for drug delivery", International Journal of Pharmaceutics, 2010, vol. 385, Issues 1-2, pp. 113-142.
Beck et al., "Spray-dried polymeric nanoparticles for pharmaceutics: a review of patents". Recent Pat Drug Deliv Formul., 2012, vol. 6, Issue 3, pp. 195-208.
Amidon et al., "A theoretical basis for a biopharmaceutic drug classification: the correlation of in vitro drug product dissolution and in vivo bioavailability", Pharmaceutical Research, 1995, vol. 12, Issue 3, 8 pages.
Bioinicia, S.L., "Nanotechnologies—Health and Safety Practices in Occupational Setting Relevant to Nanetechnologies", Report, 2008, 1-86, ISO—Technical Report.
Bohr et al., "Nanoembedded Microparticles for Stabilzation and Delivery of Drug-Loaded Nanoparticles", Current Pharmaceutical Design, 2015, 5829-5844, vol. 21.
Liu et al., "Preparation of embolic NEMs loading capecitabine", Journal of Materials Science: Materials in Medicine, 2013, 155-160, vol. 24.
Kurzrock et al., "Targeted Cancer Therapy", 2008, Abstract, 2 pages.

* cited by examiner

PHARMACEUTICAL FORMULATION WITH IMPROVED SOLUBILITY AND BIOAVAILABILITY

CROSS-REFERENCE TO RELATED APPLICATIONS AND PRIORITY

This patent application is a Divisional Application of U.S. patent application Ser. No. 17/255,680 filed Dec. 23, 2020, which claims priority from PCT Patent Application No. PCT/EP2019/067342 filed Jun. 28, 2019, which claims priority from European Patent Application No. 18382484.6 filed Jun. 29, 2018. Each of these patent applications are herein incorporated by reference in their entirety.

The invention relates to pharmaceutical formulations wherein one or more active pharmaceutical ingredient (API) is present in a sub-micron form to influence the solubility and bioavailability of the drug.

BACKGROUND ART

Most of the recent discovered pharmaceuticals present poor water solubility, leading to their low effective concentration in biofluids and poor bioavailability. Different strategies were developed to overcome this challenge, such as size reduction, modification of crystallinity, chemical alteration, solubilization in surfactant micelles or the use of pharmaceutical carriers such as polymeric micro- and nanoparticles, liposomes, solid-lipid particles, niosomes and others. Pharmaceutical carriers demonstrate a broad variety of useful properties such as longevity, targetability, intracellular penetration, reduced drug doses, which result in increased patient comfort and compliance (K. Margulis-Goshen, S. Magdassi, Nanomedicine: Nanotechnology, Biology, and Medicine 5 (2009) 274-281; V. P. Torchilin, Adv. Drug Deliv. Rev. 58 (2006) 1532-1555).

A large number of processes exist for obtaining pharmaceutical carriers (N. V. N. Jyothy et al. J. Microencapsul. 27 (2010) 187-197; C. E. Mora-Huertas et al. Int. J. Pharm. 385 (2010) 113-142). The selection of a particular technique depends on the physicochemical properties of the core, the coating used, the type of particle desired, as well as the production scale and costs. Most of the conventional techniques to produce pharmaceutical ingredients have difficulty in controlling particle size. The emulsion-based technologies allow obtaining particles in the sub-micron scale with narrow size distribution and high retention of the bioactive compound. Emulsion-based processes include emulsion polymerization, emulsion evaporation, emulsion extraction, solvent diffusion, nanoprecipitation (U.S. Pat. No. 5,049, 322) or supercritical fluid extraction of emulsions (US2004071781A1). These processes present several drawbacks such as presence of undesirable materials in the final product (residual monomers or organic solvents), production of liquid suspensions, slow extraction rate or difficulty to scale-up the process.

The spray drying technique has been widely used in the preparation of pharmaceutical powders, most often proposed as a dehydration process, but has been also used to encapsulate drugs (R. C. R. Beck et al. Recent Pat. Drug Deliv. Formul. 6 (2012) 195-208). U. Selvaraj and G. L. Messing prepared crystallites of naproxen of 35 nm inside a matrix of ethyl cellulose, with a microparticle size of 400 µm by spray drying (WO9713503-1997). However, the spray drying technique involves evaporation of the solvent using hot air. The high temperatures employed for such processing can sometimes degrade thermally labile drugs and excipients, produce large particles with broad distribution of particles sizes, impair resolubilization and can be prone to explosion if organic or alcoholic solvents are used in which low availability drugs need be dissolved.

Additionally, the recovery and handling of sub-micron particles present several technical difficulties for industry (ISO/TR 12885:2008).

Thus, due to the above-mentioned limitations of the prior art processing methods, the present invention proposes a methodology that overcomes the cited limitations by producing free flowing microparticles of excipients containing highly dispersed and distributed sub-micron size particles of low bioavailability drugs using a high throughput installation that works at room or near room temperature and that combines high voltage and nebulizing. These microparticles can then be processed using conventional technologies existing in the pharma industry to lead to pharmaceutical preparations that can be commercialized.

SUMMARY OF THE INVENTION

The present invention relates to pharmaceutical formulations in which at least one active pharmaceutical ingredient (API) is used in a sub-micron form. The bioavailability of an API can be influenced by numerous factors, including, for example, the physical form and particle size of the API in a pharmaceutical formulation, the type of excipients present in the pharmaceutical formulation together with the API, as well as the method by which the pharmaceutical formulation is prepared.

A first aspect of the present invention related to a pharmaceutical formulation comprising:

at least one active pharmaceutical ingredient (API) having low aqueous solubility or a pharmaceutically acceptable salt thereof in the form of particles of size between 1 and 800 nm, wherein said particles are encapsulated within a large microparticle of a size between 1 and 100 µm formed by a matrix comprising at least an excipient.

The active pharmaceutical ingredient (API) or pharmaceutically acceptable salt thereof is encapsulated (entrapped), highly dispersed and distributed into the particles formed by the excipients (or comprising excipients). Therefore, each particle made of excipients is a matrix where each sub-micron particles of the API or pharmaceutically acceptable salt thereof is separated out from the others by the excipient.

In a preferred embodiment, the microparticles formed by a matrix comprising at least an excipient have a size between 1 and 40 µm, more preferably between 1 and 20 µm.

In a preferred embodiment, the particles of the API or a pharmaceutically acceptable salt thereof have a size between 1 and 600 nm, more preferably between 1 and 500 nm and even more preferably between 50 and 500 nm.

The active pharmaceutical ingredient (API) having low aqueous solubility is an API that belongs to Biopharmaceutical Classification System (BCS) Class II and IV. Biopharmaceutical Classification System is an experimental model that measures permeability and solubility under prescribed conditions, developed by Amidon et al. Pharm. Res. 12 (1995) 413-420.

According to the BCS, drug substances are classified into four classes based solely on their solubility and intestinal permeability: Class I: High Solubility, High Permeability; Class II: Low Solubility, High Permeability; Class III: High Solubility, Low Permeability and Class IV: Low Solubility, Low Permeability.

Some examples of BCS Class II and IV APIs (also called pharmaceutical drugs) are: abiraterone, albendazole, axitinib, atovaquone, acetazolamide, atorvastatin calcium, amphotericin, aceclofenac, betamethasone, candesartan cilexetil, carbamazepine, carisoprodol, cefixime, ceritinib, crizotinib, celecoxib, cephalexin, clopidogrel, cefuroxime axetil, danazole, dapsone, diclofenac, dronabinol, etodolac, etoposide, ezetimib, fenofibrate, felodipine, furosemide, griseofulvin, irbesartan, itrconazole, ibufrofen, valsartan, ritonavir, paclitaxel, nilotinib, omega 3 polyunsaturated fatty acids, simvastatin, lamotrigine, lansoprazole, ketoconazole, troglitazone, nimesulide, loratadine, probucol, ubiquinone, ketoprofen, tinidazole, mesalamine, metaxalone, loperamide, methylphenidate, methylprednisolone, mycophenolate, nabumetone, nelfinavir mesylate, pioglotazone HCl, piroxicam, rifabutin, rifampin, risperidone, ritonavir, tadalafil, tacrolimus, telmisartan, vitamin D, vardenafil, triamcinolone acetonide, ofloxacin, nevirapine etc. or combinations thereof.

The omega-3 polyunsaturated fatty acids (PUFAs) can be, for example, α-linolenic acid (ALA, C18:3 n-3), eicosapentaenoic acid (EPA, C20:5n-3), and docosahexaenoic acid (DHA, C22:6 n-3), either in its ethyl ester form (EE) or triglyceride form (TG).

The low soluble drugs (APIs) are problematic for effective drug delivery in many cases, characterized by inter and intra subject variability and significant food effect. These obstacles can be overcome by usage of sub-micron particle size of the API providing, this way, better solubility and bioavailability. The encapsulation of the sub-micron API particles into microparticles allows, as a main role, to facilitate the formulation of pharmaceutical preparations containing sub-micron size APIs. In addition, this encapsulation process can also provide masking of undesirable organoleptic properties, avoid adverse effects, increase shelf-life and provide easier handling. The dosage forms and compositions of the present invention improve patient compliance by reducing dosage, which can potentially lead to less adverse effects, as well as food effect and variability reduction.

The sub-micron size particles of the API or a pharmaceutically acceptable salt thereof are highly dispersed and distributed within the matrix comprising at least an excipient. Therefore, the particles of the API are separated from each other by the material of the matrix, so that the particles of the API do not form agglomerates and hence can increase solubility and bioavailability.

In a preferred embodiment, the microparticles of a size between 1 and 100 μm consist essentially of or consist of at least an excipient encapsulating the API.

Preferably, the excipients are polymers having a molecular weight greater than the molecular weight of the active pharmaceutical ingredient or the pharmaceutically acceptable salt thereof.

In a preferred embodiment, the excipients that form the matrix of the microparticles are selected from diluents, binders, lubricants, disintegrants, glidants, surfactans, thickeners or combinations thereof.

Combinations of different APIs may be included in the formulation, including combinations in which not all of the APIs have low solubility and not all of the APIs have sub-micronized particle size (between 1 and 800 nm). When the formulation includes several APIs, at least one of them is in sub-micron ranged size and has low aqueous solubility.

A preferred embodiment of the present invention provides a pharmaceutical formulation comprising, consisting essentially of, or consisting of at least a low soluble API or a pharmaceutically acceptable salt thereof in a sub-micron ranged size between 1-500 nm, encapsulated, highly dispersed and distributed into larger microparticles between 1-20 μm comprising one or more excipients.

The microparticles containing the API (also referred as to large particles of a size between 1 and 100 μm encapsulating the API or a pharmaceutically acceptable salt thereof) are used to prepare pharmaceutical formulations in any form typically used by the pharma industry. More specifically, the pharmaceutical preparation may be in the form of a tablet, granulate, powder, capsule, thin films, patches or liquid preparation. For that, the microparticles containing the API or a pharmaceutically acceptable salt thereof are combined or mixed with additional excipients to form tablet, granulate, powder, capsule, thin films, patches or liquid preparation etc.

This additional excipients that are used to prepare the pharmaceutical formulation of the present invention in any form typically used by the pharmaceutical industry form are preferably selected from diluents, binders, lubricants, disintegrants, glidants, surfactans, thickeners or combinations thereof. Therefore, the additional excipients of the pharmaceutical composition can be the same as the excipients forming the matrix of the microparticules encapsulating the API.

In a preferred embodiment, each microparticle encapsulating the API or a pharmaceutically acceptable salt thereof in the pharmaceutical formulation comprises:
  a) 20-85% by weight of the API or a pharmaceutically acceptable salt thereof;
  b) 15-80% by weight of excipients.

In a more preferred embodiment, each microparticle encapsulating the API or a pharmaceutically acceptable salt thereof in the pharmaceutical formulation comprises, consists essentially of or consists of:
  a) 20-85% by weight of the API or a pharmaceutically acceptable salt thereof;
  b) 0-30% by weight of diluent;
  c) 0-3% by weight of glidant;
  d) 0-80% by weight of binder;
  e) 0-10% by weight of surfactant;
  f) 0-12% by weight of disintegrant;
  g) 0.4-2.5% by weight of lubricant.
  with the proviso that the sum of the components is the 100% by weight of the particle.

In a preferred embodiment, each microparticle encapsulating the API comprises, consists essentially of or consists of:
  a) 20-85% by weight of Valsartan or Abiraterone Acetate or a pharmaceutically acceptable salt thereof;
  b) 0-30% by weight microcrystalline cellulose;
  c) 0-3% by weight colloidal silicon dioxide;
  d) 0-50% by weight hydroxypropyl methylcellulose;
  e) 0-3% by weight sodium lauryl sulfate
  f) 0.4-2.5% by weight magnesium stearate.
  with the proviso that the sum of the components is the 100% by weight of the particle.

In a preferred embodiment, the pharmaceutical formulation comprises:
  a) 10-85% by weight of microparticles encapsulating the API or a pharmaceutically acceptable salt thereof;
  b) 15-90% by weight of additional excipients.

In a more preferred embodiment, the pharmaceutical formulation comprises, consists essentially of or consists of:
  a) 10-85% by weight of microparticles containing the API or a pharmaceutically acceptable salt thereof;
  b) 10-85% by weight of additional diluent;
  c) 0-3% by weight of additional glidant;

d) 0-10% by weight of additional binder;
e) 0-10% by weight of additional surfactant;
f) 0-12% by weight of additional disintegrant;
e) 0.5-3% by weight of additional lubricant.

with the proviso that the sum of the components is the 100% by weight of the pharmaceutical formulation.

The microparticles (microparticle of a size between 1 and 100 µm encapsulating the API or a pharmaceutically acceptable salt thereof) that the pharmaceutical formulation comprises are preferably obtained by the method for the industrial encapsulation of an active pharmaceutical ingredient or pharmaceutically acceptable salt thereof described in the second aspect of the invention.

The term "excipient" refers to a pharmaceutically acceptable ingredient that is commonly used in the pharmaceutical industry. Examples of categories of excipients include, but are not limited to, binders, disintegrants, lubricants, glidants, stabilizers, surfactants, fillers (diluents), thickeners. One of ordinary skill in the art may select one or more of the aforementioned excipients with respect to the particular desired properties.

Examples of disintegrants include, but are not limited to, natural, modified or pregelatinized starch, crospovidone, croscarmellose sodium, sodium starch glycolate, low-substituted hydroxypropyl cellulose, effervescent disintegrating systems and any combination thereof.

Examples of suitable binders include, but are not limited to, starch, pregelatinized starch, polyvinyl pyrrolidone (PVP), copovidone, cellulose derivatives, such as hydroxypropylmethyl cellulose (HPMC), hydroxypropyl cellulose (HPC), carboxymethyl cellulose (CMC) and their salts and or any combination thereof.

Examples of suitable diluents include, but are not limited to, starch, microcrystalline cellulose, cellulose, lactose, sucrose, xylitol, mannitol, dextrins, maltose, polyols, fructose, guar gum, sorbitol, magnesium hydroxide, dicalcium phosphate and any combinations thereof.

Examples of the lubricant include, but are not limited to, magnesium stearate, calcium stearate, stearic acid, talc, sodium stearyl fumarate and any combination thereof.

Examples of glidant include, but not limited to, colloidal silica, silica gel, precipitated silica, and anycombinations thereof.

Surfactants include non-ionic, anionic and cationic surfactants. Examples of surfactants include, but not limited to, sorbitan esters and polysorbates (Span™, Tween™, TEGO™), poloxamer, sodium lauryl sulfate, Meglumin, poly(vinyl pyrrolidone), polyglycerol, polyricinoleate, poly(vinyl alcohol), Pickering emulsifiers and block copolymers.

The term "encapsulated" in the present invention, when referring to the API, means that the API is within the particle (matrix) made of or comprising excipients or it is entrapped or embedded highly dispersed and distributed in the particle made of or comprising excipients.

As used herein, the term "particle size" refers to the diameter of a spherical particles (particles are preferably spherical) or refers to equivalent diameter of a non-spherical particle. "Equivalent diameter" refers to the maximum dimension of a non-spherical particle. Particle size measurements are commonly performed using scanning electron microscopy, transmission electron microscopy, optical microscopy or light scattering.

The term "consisting essentially of as used herein is intended to denote a formulation comprising the components as specified as well as other components in trace amounts wherein the presence of the other components does not change the essential characteristics of the specified subject matter.

A second aspect of the present invention relates a method for the industrial encapsulation of an active pharmaceutical ingredient or pharmaceutically acceptable salt thereof.

The method to prepare sub-micron particles (1 and 800 nm) of at least one active pharmaceutical ingredient or pharmaceutical acceptable salt thereof encapsulated into microparticles (1 and 100 µm) comprising excipients, is characterized in that it is carried out in a facility comprising:
    an injection unit, which is preferably a nebuliser or an electronebuliser,
    a drying unit, which is arranged after the injection unit, and
    a collection unit, arranged after the drying unit.

The method comprises the following stages:
a) preparing an emulsion comprising:
    at least one active pharmaceutical ingredient (API) or pharmaceutically acceptable salt thereof to be encapsulated,
    one or more excipients
    at least two non-miscible, partially miscible solvents or two miscible solvents that by solubilizing the API or the excipients become non-miscible or partially miscible;
b) forming droplets from the emulsion obtained in stage (a) in the presence of an injection gas flow;
c) drying the droplets obtained in stage (b) in the drying unit at a controlled temperature to obtain microparticles; and
d) collecting the microparticles obtained in stage (c) by means of the collection unit.

The solvents can be polar or non-polar. The non-polar solvents (e.g. organic or oil-based) are immiscible, partially miscible or miscible with the polar solvent, with the condition that miscible solvents become immiscible or partially miscible due to the presence of the API or the excipients. Preferred solvents for use in the invention include, for example, water, alcohol (preferably ethanol or isopropanol), toluene, ethyl acetate, acetone, methylene chloride, chloroform, dimethyl sulfoxide (DMSO), dimethyl formamide (DMF), tetrahydrofuran (THF), deep eutectic solvents, natural deep eutectic solvents, other organic and inorganic solvents, and combinations thereof selected on the basis of their chemical inertness and sufficient solubility power/dispersability for the solute.

A variety of emulsions types are suitable for use with the present invention. For example, oil-in-water (O/W), water-in-oil (W/O), water-in-oil-in-water (W/O/W), oil-in-water-in-oil (O/W/O), oil-in-oil (O/O), and Pickering emulsions.

The term "Pickering emulsion" refers to an emulsion that is stabilized by solid particles (for example hydroxyapatite, silica, clay, magnetic nanoparticles) which adsorb onto the interface between the two phases.

The size of the droplets (emulsion micelles) obtained in step a) can depend upon the agitation speed or the degree of homogenization of the emulsifier and the concentration or solvent or the solutes. Generally, a higher degree of homogenization, higher concentrations tend to produce smaller droplets or micelles. The emulsifier is preferably a dispersator, ultrasonic horn, microfluidizer, static mixer, colloid mill, fluid energy mill, turbine mixer, or a spontaneous emulsification technique.

Preferably, the stage c) is carried out at temperature between 1-45° C.

In a preferred embodiment of the invention, the excipient used in stage a) comprises a surfactant. The surfactant is useful to extend the stability of the emulsion. They are also very used to avoid agglomerations of the particles of the API.

In a preferred embodiment of the invention, the stage b) of forming droplets is carried out by applying a voltage of between 0.1 kV and 500 KV to the emulsion and injection gas flow at the outlet of the injection unit. More preferably, stage b) of forming droplets is carried out by applying a voltage of between 5 KV and 15 kV to the emulsion and injection gas flow at the outlet of the injection unit.

In a preferred embodiment of the invention, the stage b) of forming droplets is carried out by applying a voltage in alternating current.

This method allows obtaining an active pharmaceutical ingredient (API) or pharmaceutically acceptable salt thereof in a sub-micron particle form encapsulated within microparticles comprising excipients.

The resulting blend of the API entrapped into the microparticles with additional excipients is being used for the final dosage form manufactured by any of the conventional pharmaceutical processes. These processes may comprise direct compression, dry granulation, wet granulation process or others.

The proposed formulations may be dry-granulated or wet-granulated, or the blends (blends formed microparticles encapsulating the API and additional excipients) may be directly compressed into tablets, filled into capsules or sachets.

For pharmaceuticals, the type of processing utilized often depends upon the properties of the drug, the chosen excipients, and the dosage form, e.g., particle size, blending compatibility, density, and flowability.

In one embodiment, the invention encompasses a method of making tablets or capsules by wet granulation comprising: providing a mixture of encapsulated API (microparticules encapsulating the API), at least one diluent, binder, and granulation liquid; blending the mixture to obtain a wet granulate; drying the wet granulate to obtain a dried granulate; and milling the dried granulate. The method may further comprise combining the dried granules with one or more additional excipients, adding at least one lubricant. The resulting granules may be subsequently encapsulated into capsules, compressed into tablets, or filled into sachets to form solid or liquid oral dosage forms. The tablets may further be coated.

There are economic advantages in the dry compression of formulations over wet granulation, because the dry compression requires less equipment, lower power consumption, less time, and less labour. Also, dry compression avoids the use of organic solvents during the preparation of the formulations.

An additional method of the finished product manufacturing is a dry granulation process. This method of making a formulation comprises providing a mixture of encapsulated API, at least one diluent, binder, disintegrant; blending the mixture to obtain a homogeneous mixture; optionally adding at least one lubricant to the homogeneous mixture; and dry compressing the homogeneous mixture into the formulation. The formulation can be in the shape of a tablet, a slug, or a compact. The method may further comprise milling the slug or compact into a granulate, adding at least one lubricant to the milled granulate, and compressing the milled granulate into tablets, encapsulating into capsules, or filling into sachets to form solid or liquid oral dosage forms.

The alternative method of making the tablets or capsules is by direct compression of dry formulations into tablets or filling into capsule or sachets. The dry compression, however, is generally limited to those circumstances in which the active ingredient has physical characteristics suitable for forming pharmaceutically acceptable tablets. These physical characteristics include, but are not limited to, good flowing properties and compressibility. The encapsulated API made by the invention, would be suitable for the direct compression or direct filling process, other manufacturing processes can be applicable for such encapsulated API as well.

Regarding the encapsulation facility, preferably it comprises at least:
one injection unit having at least:
  one inlet for an emulsion;
  one inlet for injection gas; and
  one outlet for droplets through which sprayed droplets of emulsion are released,
one drying unit arranged after the injection unit and comprising at least:
  one inlet for drying gas;
  one inlet for droplets;
  one longitudinal receptacle through which the droplets with the drying gas move until the solvent of the droplets evaporates, forming microparticles; and
  at least one outlet for microparticles and drying gas through which the microparticles and drying gas that drags the evaporated solvent with it are released from the receptacle;
one collection unit arranged after the drying unit, which is configured to separate the microparticles generated from the drying gas.

The facility enables industrial amounts of microcapsules of maintaining or increasing protection (protection of the API inside the microcapsule), provided by other low-production techniques, such as electrospraying and flow focusing.

The injection unit comprises an injector, at the inlet of which an emulsion comprising the API (or a pharmaceutically acceptable salt thereof) to be encapsulated, the encapsulating material (excipients), solvents and necessary additives (e.g. typically surfactants, thickeners or Pickering emulsifiers) is introduced. Throughout the specification, when reference is made to the emulsion (mixture of immiscible liquids) to be injected.

The injection unit projects droplets whose size can be focused or controlled more efficiently through the application of an electric field at the injector outlet (in this exemplary embodiment, the injection unit can be an electronebuliser). To this end, in one exemplary embodiment, the injection unit comprises an electrode, typically circular, which is arranged at the injector outlet.

In the case in which the injection unit comprises an electric field at the injector outlet, the emulsion is electrically charged during spraying upon penetrating said electric field which is generated by applying high voltage, both in alternating current (AC) and direct current (DC). Adding the electric field enables better control over the size and monodispersity of the sizes of the droplets generated in the injector unit. Since APIs are going to be encapsulated and hot air is not going to be applied for drying, the droplets generated must be very small in order to reduce subsequent drying times.

In this facility hot air is not applied at the injector outlet of the injection unit. Therefore, better stability and protection results are achieved in terms of encapsulation of APIs.

It is a continuous process that is executed in a single step under controlled, typically room temperature conditions.

The injection unit comprises a nebuliser-, sprayer- or aerosol-type injector, including pneumatic devices, piezoelectric devices, ultrasonic devices, vibratory devices, etc. In an embodiment of the present invention, the injection unit comprises a pneumatic nebuliser of the type comprising an inlet for a liquid emulsion and two inlets for injection gas. In this exemplary embodiment, the injection unit comprises two inlets for injection gas, of which one inlet for injection gas is arranged coaxially to the emulsion inlet and an additional inlet for injection gas is arranged with a certain degree of inclination to the emulsion inlet.

That is, one of the inlets for injection gas is arranged such that the injection gas flow is projected in a coaxial direction to the emulsion flow, as in any nebuliser, and the other inlet is arranged such that the injection gas flow is projected at a certain angle with respect to the emulsion flow, impacting against the liquid jet flow. This enables greater reduction in drop size. In this case, the facility may be used with a gas flow that can be air, nitrogen or other gas and mixtures thereof. For example, an inert gas would be used to work in a protective atmosphere or when using a flammable solvent.

As described, the injection unit projects droplets whose size depends on the type of injector, specifically in the preferred case in which the injection unit comprises a nebuliser such as that described, the size depends on the flow rate of a emulsion current, on the flow rate of an injection gas current and on the properties of the emulsion, mainly surface tension, conductivity and viscosity.

Additionally, the present invention proposes the use of an external electric field for greater control of the size of the droplets and their monodispersity. For this objective in one exemplary embodiment, the injection unit comprises an electrode, typically circular, arranged right at the injector outlet. The liquid, during spraying, is electrically charged upon penetrating said electrode, which is working at high voltage, both in direct and alternating current.

In the drying unit, the droplets formed in the injection unit are dried at a controlled temperature. During the movement of the droplets through the drying unit, the solvent of the emulsion with which the microcapsules have been formed evaporates. After circulating completely through the drying unit, the solvent evaporates completely, giving rise to the desired microcapsules which are subsequently collected by the collection unit. It should be noted that the unit can dry and encapsulate at a controlled temperature, typically at ambient or sub-ambient temperature, without the need to apply heat at a high temperature to vaporise the solvent. In the case in which an API at ambient temperature is used, the facility and method make it possible to work at sub-ambient temperature, such as for example 5° C.

The drying unit comprises a receptacle. The injection unit and a drying gas inlet are at one end of said receptacle. The collection unit is at the opposite end. The drying gas is introduced in the drying unit at a controlled temperature. The drying gas may be air, nitrogen or other gas and mixtures thereof.

The arrangement of the drying unit with respect to the injection unit may be both coaxial thereto and at any angle of inclination therebetween. The present invention preferably proposes a coaxial arrangement. The drying gas is introduced in the drying unit at a controlled temperature, typically at ambient temperature. Since the drying gas is introduced in the drying unit in a certain direction, it drags the droplets generated in the injection unit with it. As it circulates through the drying unit, the solvent in the droplets evaporates, thereby giving rise to the desired microcapsules.

The geometry of the drying device a priori may be any which allows an adequate residence time for drying the drops. An optimum geometry would be a cylinder with a variable circular cross-section, with an increasing cross-section from the inlet to the outlet. This enables greater dragging in the area in which the drops are largest and this allows longer residence time for a certain length.

In another exemplary embodiment, the facility comprises a drying unit comprising a secondary inlet, arranged perpendicularly to its longitudinal axis. These drying units comprise a sleeve and a secondary gas flow. This secondary gas flow is injected in a direction perpendicular to the surface of the drying unit through holes or pores arranged on the surface of the drying unit. This makes it possible to reduce loss of material from adhesion to the walls of the drying unit. The secondary gas may be air, nitrogen or other gas and mixtures thereof.

The drying gas flow must be sufficient to remove all the solvent injected from the injection unit.

That is, if, for example, air from outside the facility is used as the drying gas and the method is being carried out on a rainy day, with a high degree of humidity, the amount of drying gas required to evaporate a fixed solvent volume will be greater than if the method is carried out on a dry day (since the outside air will have a lower relative humidity).

Likewise, a smaller drying unit cross-section size is selected, which generally has a cylindrical configuration, when wanting to achieve greater dragging and collection of microparticles. This is because if the drying gas flow rate is maintained and the drying unit cross-section is decreased, the dragging speed through the inside of said drying unit increases.

Furthermore, it should be noted that higher gas speeds (obtained, for example, by decreasing the size of the cross-section of the drying unit as explained previously) give rise to shorter residence times and, therefore, shorter drying times. This could make it difficult to dry larger microparticles.

Therefore, the facility is designed so as to have a specific compromise emulsion in which dragging speed and residence time for each emulsion are optimised. The facility will be designed maintaining compromise dimensions to optimise dragging speed and drying time in accordance with the emulsion used for encapsulation. Drying time is also called residence time, since it relates to the time during which the droplets remain in the drying unit.

The design of the drying unit depends on the solvent used and on the API to be encapsulated, since both factors strongly influence the size of the drop generated by the injection unit and the evaporation kinetics thereof. The optimum drying unit diameters and lengths that enable optimum speeds and residence times for, for example, a facility with a manufacturing yield of approximately 1 kg/h of dry or encapsulated product typically range, but are not limited to, between 2 and 200 cm in diameter and between 20 cm and 20 m in length, respectively. Larger industrial facilities may use foreseeably greater diameters and lengths.

The proposed facility is therefore optimal for industrial use due to its high yield and makes it possible to carry out the method for obtaining microcapsules of APIs continuously and in a single step.

With the aim of controlling the evaporation of the solvent more efficiently, the facility, more specifically the drying unit, may operate at different pressures, even in a vacuum.

The collection unit enables the efficient separation of the microcapsules generated from the drying gas. The collection unit may comprise at least one cyclonic separation, centrifugal separation or filtration device, with or without electrostatic charge. The collection unit is preferably a cartridge filter collector or a cyclonic collector. In one exemplary embodiment, the collection unit comprises a cyclone collector and a cartridge filter arranged in series. This makes it possible to collect large microparticles in the cyclone collector and smaller microparticles in the cartridge filter collector.

In the case of using a flammable solvent, inert gases, typically nitrogen, will preferably be used, and the facility in which the method is carried out must be manufactured from ATEX-classified materials and units, comprising venting and suppression devices.

In the case that the device is used to obtain a dry product or aseptic encapsulation, the injection gas and drying gas must be filtered, typically making them pass through a HEPA H14 filter or similar, or sterilised, typically by means of exposure to ultraviolet light, ethylene oxide, radiation, etc., or a combination thereof. In this case, both the preparation of the emulsion and handling of the collected product are carried out in a clean room sterile facility or similar.

Likewise, in a preferred embodiment, the collection unit comprises a solvent condensing device, arranged at the drying gas outlet, downstream from the collection unit. In another exemplary embodiment, the drying gas collected at said drying gas outlet is recirculated to resupply the injection unit and/or drying unit. Typically, the recovery of the solvent or the closed-loop resupply thereof is of special interest when the solvent or drying gas used is expensive or for security or sterility reasons. The facility may also include a device for pre-drying the incoming gas to facilitate drying of the droplets or the closed-loop recirculation thereof. This case is a preferred embodiment when the drying gas is ambient air.

In summary, the present invention provides a pharmaceutical formulation containing pharmaceutical active ingredient having improved solubility and supra-bioavailability. In such the case, a lower dosage strength can be administrated.

The sub-micron size particles of a non-water soluble drug (API) can be obtained in a solid form free of agglomeration that can be later on used to obtain the finished product, in which by virtue of the small size of the drug particles within the product, better bioavailablility can be achieved.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and figures are provided by way of illustration and are not intended to be limiting of the present invention.

DETAILED DESCRIPTION OF THE DRAWINGS

Figure 1A:
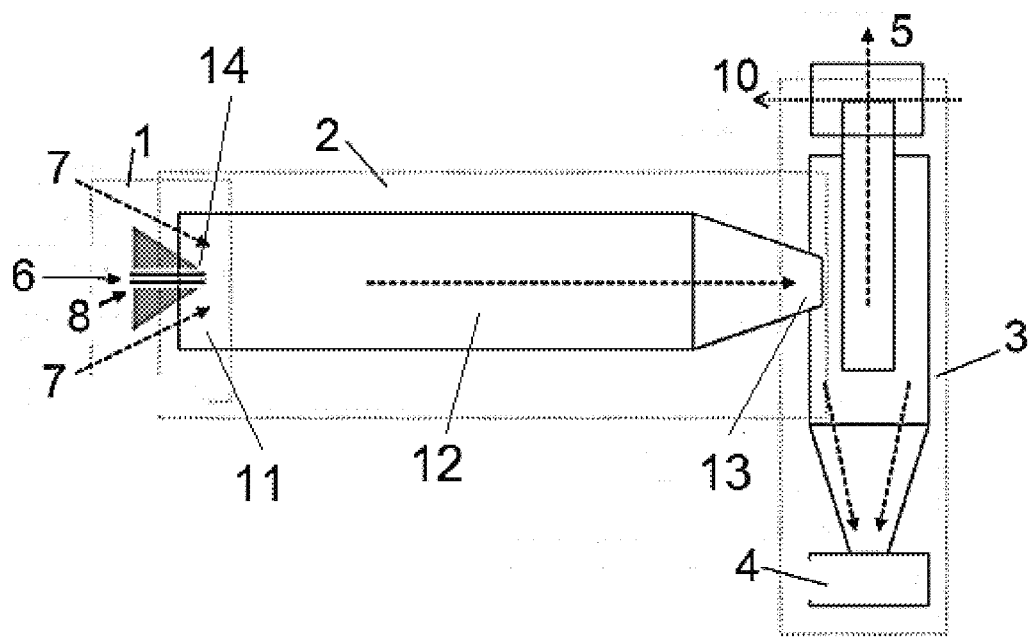
FIG. 1. 1a. Shows an exemplary embodiment of the facility for industrial encapsulation of an API (or pharmaceutically acceptable salt thereof) wherein the injection unit (1), drying unit (2) and collection unit (3) can be seen. 1b. Shows another exemplary embodiment of the facility for industrial encapsulation of an API (or pharmaceutically acceptable salt thereof) comprising an electric circuit (9) arranged at the droplet outlet (14) of the injection unit (1).
Figure 1B:
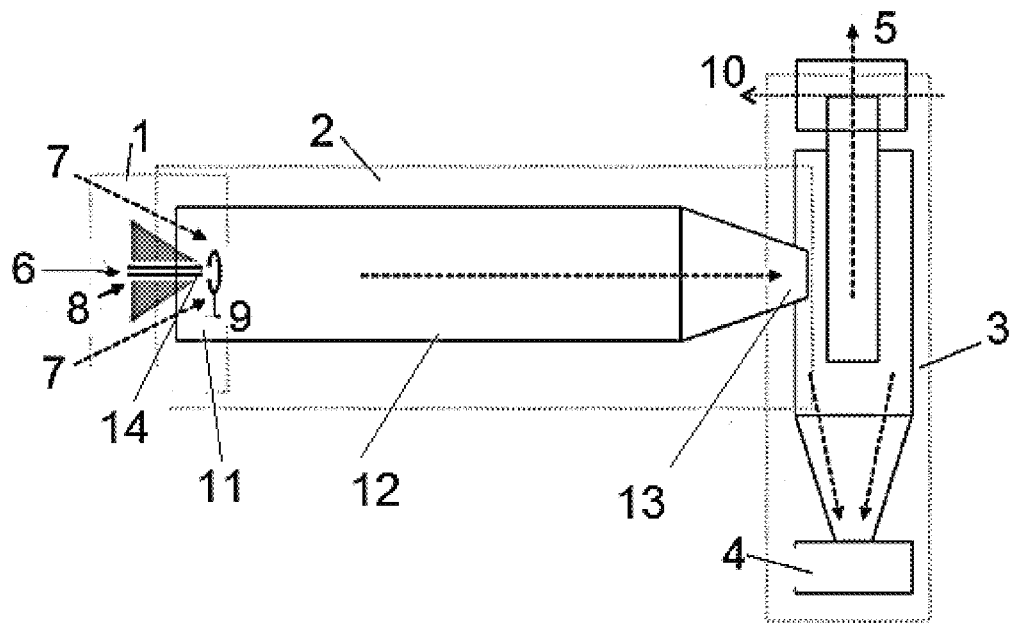
Figure 2:
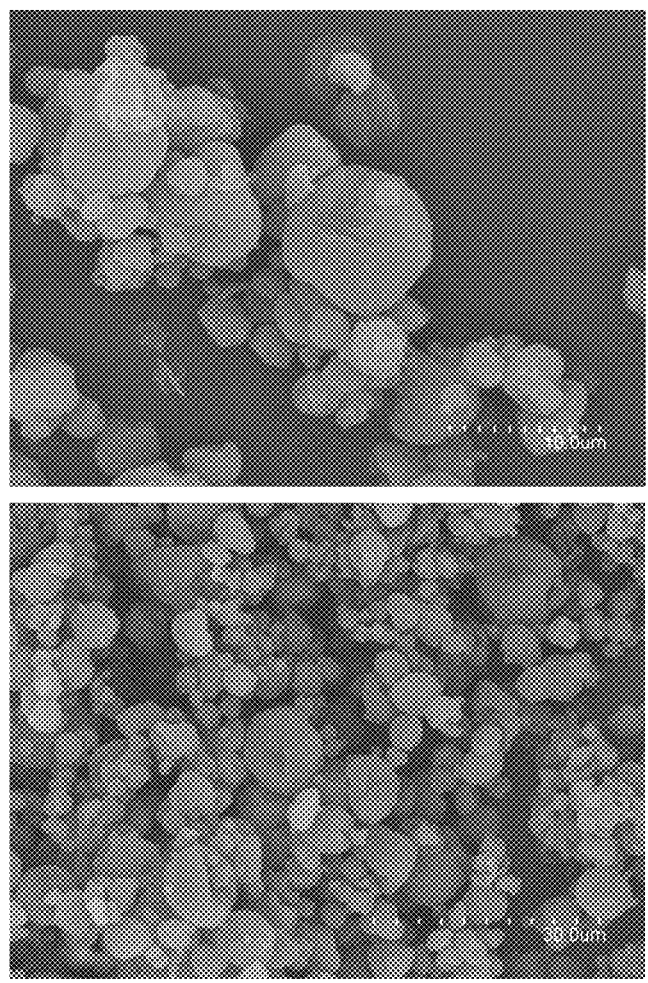
FIG. 2. Shows the SEM images of HPMC-valsartan microparticles obtained by the electro-nebulizer in example 1.
Figure 3:
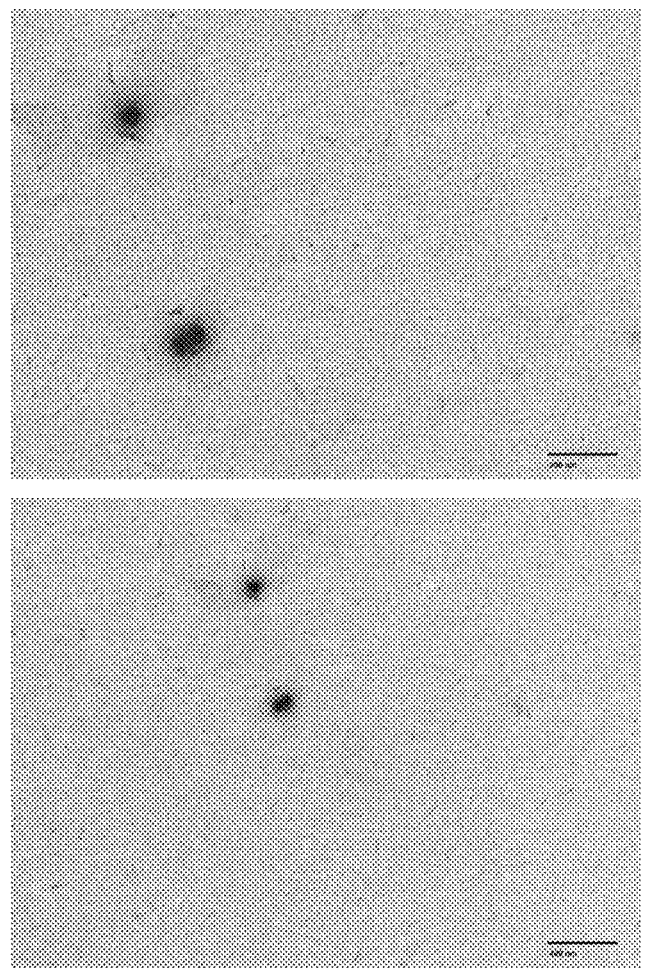
FIG. 3: Shows the TEM images of valsartan particles obtained by the electro-nebulizer, after dissolving the polymer in cold water in example 1.
Figure 4:
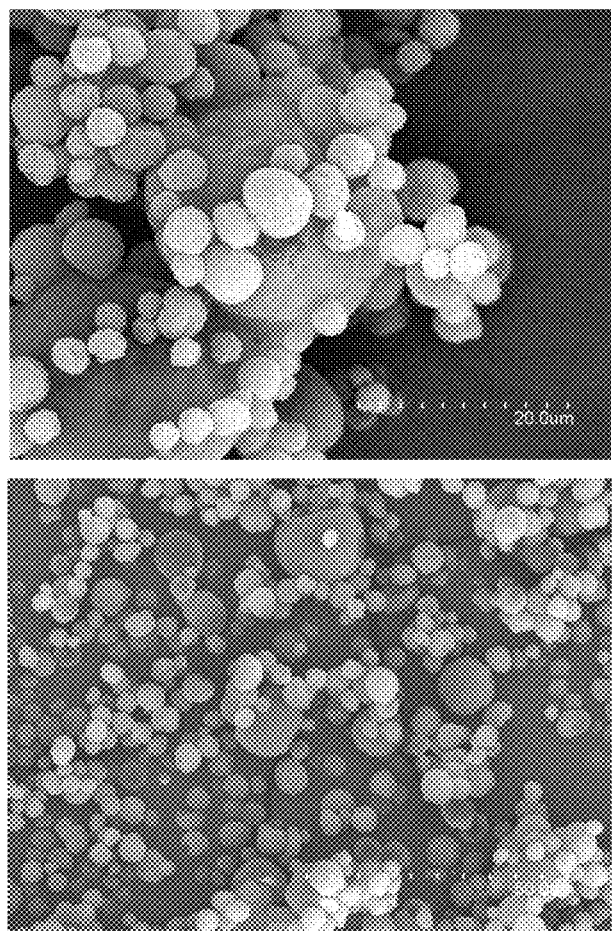
FIG. 4. Shows the SEM images of HPMC-valsartan microparticles obtained by the electro-nebulizer in example 2.

As shown in FIG. 1, the facility for carrying out the method of encapsulation of an API comprises at least:
one injection unit (1) comprising at least one injector with at least one inlet for a emulsion (6) (which already includes valsartan to be encapsulated, the encapsulating material in the case that it is used for an encapsulation process, a solvent and necessary additives), an inlet for the injection gas (8) and an outlet for droplets (14) for the emulsion that exits sprayed in droplets;
one drying unit (2) arranged after the injection unit (1) and comprising at least one drying gas inlet (7) and an inlet for the droplets (11) that exit the injection unit (1); and comprising a longitudinal receptacle (12) which preferably has a cylindrical configuration, and which is arranged with its longitudinal direction horizontal and which has sufficient length to allow the evaporation of all the solvent of the droplets; and has a microparticles and drying gas outlet (13) through which microparticles pass (which are the droplets without the solvent, which has evaporated during its circulation through the drying unit);
one collection unit (3) arranged after the drying unit, which is configured to separate the microparticles generated from the drying gas (it drags the solvent which has evaporated in the drying unit) and comprises an outlet for said generated microparticles (4) and an outlet for the drying gas (5).

In one exemplary embodiment of the invention, the collection unit further comprises a solvent condensing device (10), arranged at the drying gas outlet (5), downstream from the collection unit (3). In another exemplary embodiment, the facility may comprise a drying gas recirculation device that makes it possible to redirect the drying gas towards the injection unit (1) and/or the drying unit (2).

In one exemplary embodiment, the injector of the injection unit is a nebuliser consisting of a sprayer such as that described above. The injection gas flow rate, in one exemplary embodiment, is between 1 and 500 L/min. The flow rate of the injected liquid, which is in the form of emulsion, ranges preferably between 1 ml/h and 50 L/h.

Figure 5:
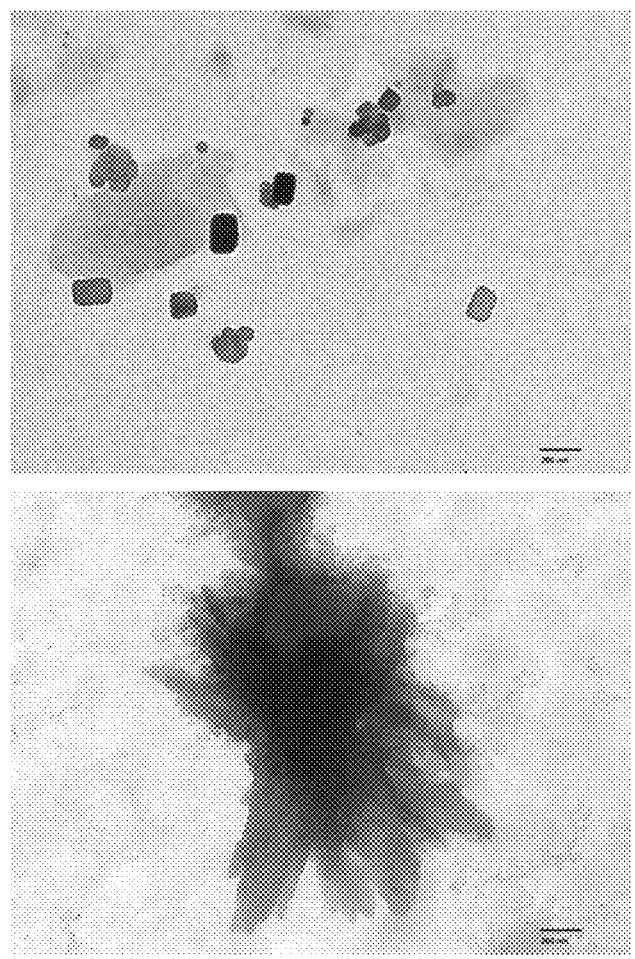
FIG. 5. Shows the TEM images of valsartan particles obtained by the electro-nebulizer, after dissolving the polymer in cold water in example 2.

In one exemplary embodiment, the facility additionally comprises a high-voltage electric circuit (9) at the outlet of the injection unit (1). The voltage used in the circuit depends on the flow rate of the injected emulsion and ranges between 100 V and 500 KV. The effect achieved is that of charging the emulsion, focusing the droplet beam and collaborating in the formation of the droplets, improving control over the size thereof. It also influences the monodispersity of the droplets, since it generates a more homogeneous size distribution. A high monodispersity may be essential to the final product, since it enables greater homogeneity in the protection or release of the API that has been encapsulated and, therefore, greater control over the encapsulation process.

In one exemplary embodiment, the drying gas flow rate ranges between 10 and 100,000 $m^3$/h.

To this end, in these cases the facility may additionally comprise a device for pre-drying the drying gas in order for said drying gas introduced in said unit to be drier, thereby increasing the yield of the facility. In those cases where ethanol, isopropanol and other non-aqueous solutions are used drying is easier because the drying gas, typically air, does not include a solvent. Therefore, the drying gas is free from ethanol and, therefore, does not affect the speed of evaporation of the ethanol in the drying unit.

In order to control the evaporation of the solvent in the facility more efficiently, the drying unit further comprises, in one exemplary embodiment, a pressure control device that makes it possible to work at different pressures, even in a vacuum.

Preferably, the facility is designed to obtain a microparticle size ranging between 1 and 50 μm in diameter. For typical drying flow rates between 10 and 100,000 $m^3$/h, the optimum diameters and lengths of the drying unit range between 20 and 200 cm in diameter and between 20 cm and 20 m in length. In an exemplary embodiment detailed below, the drying unit comprises a cylindrical receptacle 60 cm in diameter and 2 m in length with cone-shaped inlets and outlets.

Example 1

HPMC-valsartan microparticles (percentage of API in the particle is of 30% by weight)

In this example, the production of hydroxypropyl methyl cellulose or hypromellose (HPMC) microparticles containing sub-micron sized valsartan particles is described, using the electro-nebulizer technique, with a percentage of API in the particle of 30% by weight.

Emulsion Preparation:

In this case, an oil in water (O/W) emulsion was used, with a ratio organic phase: aqueous phase of 30:70. In a first step, the aqueous phase of the emulsion is prepared. The polymer (HMPC) is dissolved in cold deionized water with a concentration of 20 mg/mL. 10 mg/ml of TEGO (TEGO® SML sorbitan fatty acid ester) is added to this mixture. The organic phase of the emulsion consisted of 30 mg/ml of valsartan in chloroform. The organic phase is slowly added over the aqueous phase and stirred in the ultraturrax for 5 min at 17,000 rpm, followed by 1 min of ultrasounds to achieve a homogeneous size distribution of the micelles of the emulsion. During the stirring, the emulsion is maintained in a cold bath to prevent emulsion temperature from rising.

Electro-Nebulizer Process:

Once the emulsion has been obtained, it is immediately used to generate microparticles by the electro-nebulizer technology. The emulsion is introduced in the drying chamber by means of the injection equipment at a flowrate of 10 mL/min. This injection equipment has an electro-nebulizer to generate an aerosol of the emulsion and, thus, guarantees an adequate evaporation of the solvent. This electro-nebulizer operates with a compressed air flow rate of 10 L/min and a voltage of 10 kV. The aerosol drops are dried by means of 85 $m^3$/h of process air, in co-current mode, and at room temperature. The dried microparticles are collected on a cyclone.

Particle Characterization:

The morphology of the microparticles obtained is studied by SEM. The HPMC-valsartan microparticles have a medium size of 4.1 μm (±2.0). They are shown in FIG. 2.

In order to observe the morphology of the drug inside the HPMC microparticle, the polymer (HMPC) was dissolved in cold deionized water and the morphology of the drug is studied by Transmission Electron Microscopy (TEM). The drug exhibits a submicron size needle shape, shown in FIG. 3.

The obtained encapsulated Valsartan particles are being used for the finished product manufacturing by usage of conventional pharmaceutical techniques.

Example 2

HPMC-valsartan microparticles (percentage of API in the particle is of 63% by weight)

In this example, the encapsulation of valsartan in HPMC is described, using the electro-nebulizer technique, with a percentage of API in the particle of 63% by weight.

Emulsion Preparation:

An oil in water (O/W) emulsion was used, with a ratio organic phase: aqueous phase of 30:70. In a first step, the aqueous phase of the emulsion is prepared. The polymer is dissolved in cold deionized water with a concentration of 20 mg/mL. 10 mg/ml of TEGO (TEGO® SML sorbitan fatty acid ester) is dissolved in this mixture. The organic phase of the emulsion consisted of 120 mg/ml of valsartan in ethanol 85%. The organic phase is slowly added over the aqueous phase and stirred in the ultraturrax for 5 min at 17,000 rpm, followed by 1 min of ultrasounds to achieve a homogeneous size distribution of the micelles of the emulsion. During the stirring, the emulsion is maintained in a cold bath to prevent emulsion temperature from rising.

Electro-Nebulizer Process:

Once the emulsion has been obtained, it is immediately used to generate microparticles by the electro-nebulizer method. The emulsion is introduced in the drying chamber by means of the injection equipment at a flowrate of 10 mL/min. This injection equipment has an electro-nebulizer to generate an aerosol of the emulsion and, thus, guarantee an adequate evaporation of the solvent. This electro-nebulizer operates with a compressed air flowrate of 10 L/min and a voltage of 10 kV. The aerosol drops are dried by means of 85 $m^3$/h of process air in co-current mode at room temperature. The dried microparticles are collected on a cyclone.

Particle Characterization:

The morphology of the microparticles obtained is studied by SEM. The HPMC-valsartan microparticles are spheres with a medium size of 5.0 μm (±4.1). They are shown in FIG. 4.

In order to observe the morphology of the drug inside the HPMC microparticle, the polymer was dissolved in cold deionized water and the morphology of the drug is observed by TEM. The drug exhibits a submicron size needle shape which is shown in FIG. 5.

The obtained encapsulated Valsartan particles are being used for the finished product manufacturing by usage of conventional pharmaceutical techniques. The final pharmaceutical formulations is in the form of a tablet, granulate, powder, capsule or other.

Example of a Pharmaceutical Composition:
- a) encapsulated valsartan 111 mg (microparticles of HPMC encapsulating valsartan)
- b) microcrystalline cellulose 40 mg
- c) colloidal silicon dioxide 4 mg
- d) sodium lauryl sulfate 1 mg
- e) magnesium stearate 1.6 mg
- f) Opadry® White 5 mg A mixture was made of encapsulated valsartan, microcrystalline cellulose, colloidal silicon dioxide, sodium lauryl sulfate with the above-mentioned quantities. The mixture was blended for 20 minutes. Magnesium stearate was sieved and added to the blended mixture and blended for an additional 5 minutes. Thereafter, the mixture was compressed into tablets using a Fette tableting press to have a suitable hardness and a friability of less than 1.0%. The tablet cores were coated with ready to use coating mixture Opadry.

Example 3

HPMC-valsartan microparticles (percentage of API in the particle is of 82% by weight)

In this example, the encapsulation of valsartan in HPMC is described, using the electro-nebulizer, with a percentage of API in the particle of 82% by weight.

Emulsion Preparation:

In this case, an oil in water emulsion (O/W) was used, with a ratio organic phase: aqueous phase is of 30:70. In a first step, the aqueous phase of the emulsion is prepared. The polymer with a concentration of 10 mg/mL was dissolved in cold deionized water. 1 mg/ml of TEGO (TEGO® SML sorbitan fatty acid ester) is dissolved in this mixture. The organic phase of the emulsion consisted of 120 mg/ml of valsartan in ethanol 85%. The organic phase is slowly added over the aqueous phase and stirred in the ultraturrax for 5 min at 17,000 rpm, followed by 1 min of ultrasounds to achieve a homogeneous size distribution of the micelles of the emulsion. During the stirring the emulsion is maintained in a cold bath, to prevent emulsion temperature from rising.

Electro-Nebulizer Process:

Once the emulsion has been obtained, it is immediately used to generate microparticles by the electro-nebulizer method. The emulsion is introduced in the drying chamber by means of the injection equipment at a flow rate of 10 mL/min. This injection equipment has an electro-nebulizer to generate an aerosol of the emulsion and, thus, guarantee an adequate evaporation of the solvent. This electro-nebulizer operates with a compressed air flow rate of 10 L/min and a voltage of 10 kV. The aerosol drops are dried by means of 85 m$^3$/h of process air in co-current mode at room temperature. The dried microparticles are collected on a cyclone.

Figure 6:
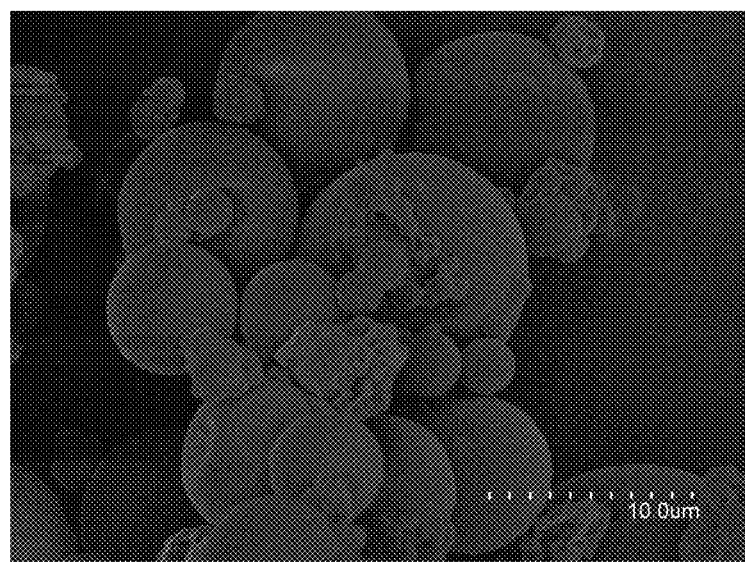
FIG. 6. Shows the SEM images of HPMC-valsartan microparticles obtained by the electro-nebulizer in example 3.

Particle Characterization:

The morphology of the microparticles obtained is studied by SEM. The HPMC-valsartan microparticles are spheres with a medium size of 6.1 μm (±3.3). They are shown in FIG. 6.

Figure 7:
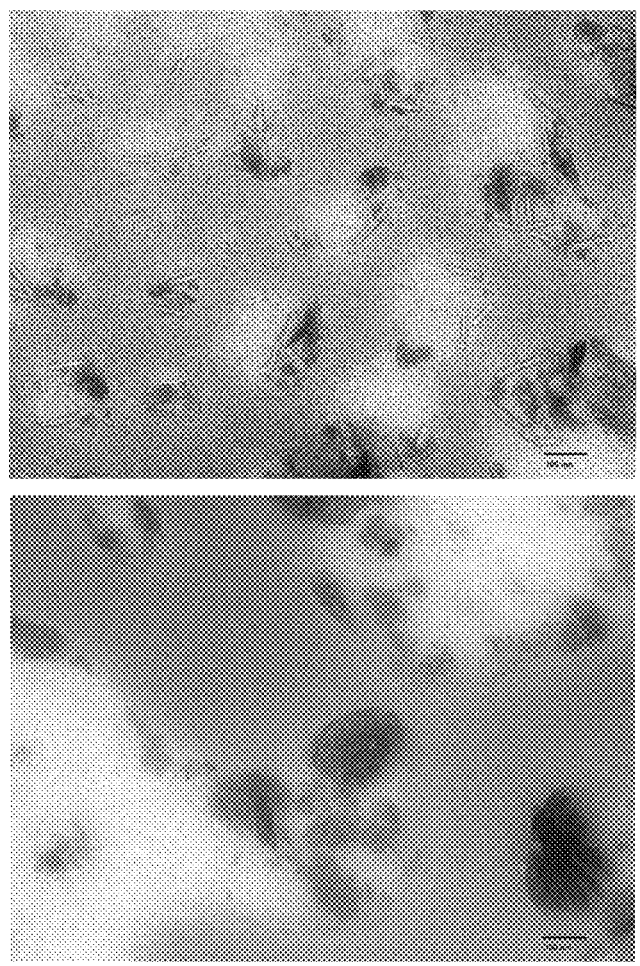
FIG. 7. Shows TEM images of valsartan particles obtained by the electro-nebulizer, after dissolving the polymer in cold deionized water in example 3.

In order to observe the morphology of the drug inside the HPMC microparticle, the polymer was dissolved in cold deionized water and the morphology of the drug is observed by TEM. The drug shows a submicron size needle shape, which is shown in FIG. 7.

The obtained encapsulated Valsartan particles are being used for the finished product manufacturing by usage of conventional pharmaceutical techniques.

Example 4

HPMC-valsartan microparticles (percentage of API in the particle is of 71% by weight)

In this example, the encapsulation of valsartan in HPMC is described, using the electro-nebulizer, with a percentage of API in the particle of 71% by weight.

Emulsion Preparation:

In this case, an oil in water emulsion (O/W) was used, with a ratio organic phase: aqueous phase of 30:70. In a first step, the aqueous phase of the emulsion is prepared. The polymer with a concentration of 20 mg/mL was dissolved in cold deionized water. 1 mg/ml of TEGO (TEGO® SML sorbitan fatty acid ester) is dissolved in this mixture. The organic phase of the emulsion consisted of 120 mg/ml of valsartan in ethanol 85%. The organic phase is slowly added over the aqueous phase and stirred in the ultraturrax for 5 min at 17,000 rpm, followed by 1 min of ultrasounds to achieve a homogeneous size distribution of the micelles of the emulsion. During the stirring, the emulsion is maintained in a cold bath to prevent emulsion temperature from rising.

Electro-Nebulizer Process:

Once the emulsion has been obtained, it is immediately used to generate microparticles by the electro-nebulizer. The emulsion is introduced in the drying chamber by means of the injection equipment at a flowrate of 10 mL/min. This injection equipment has an electro-nebulizer to generate an aerosol of the emulsion and, thus, guarantees an adequate evaporation of the solvent. This electro-nebulizer operates with a compressed air flowrate of 10 L/min and a voltage of 10 kV. The drops of the aerosol are dried by means of 85 m$^3$/h of process air, in co-current mode, and at room temperature. The dried microparticles are collected on a cyclone.

Figure 8:
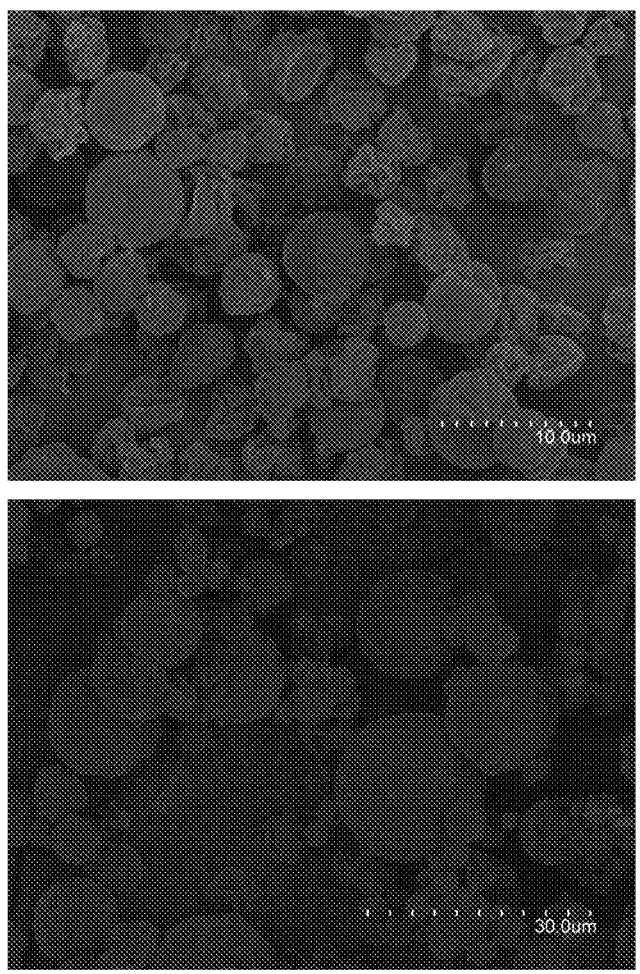
FIG. 8. Shows SEM images of HPMC-valsartan microparticles obtained by the electro-nebulizer in example 4.

Particle Characterization:

The morphology of the microparticles obtained is studied by SEM. The HPMC-valsartan microparticles are spheres with a medium size of 6.1 μm (±3.3). They are shown in FIG. 8.

Figure 9:
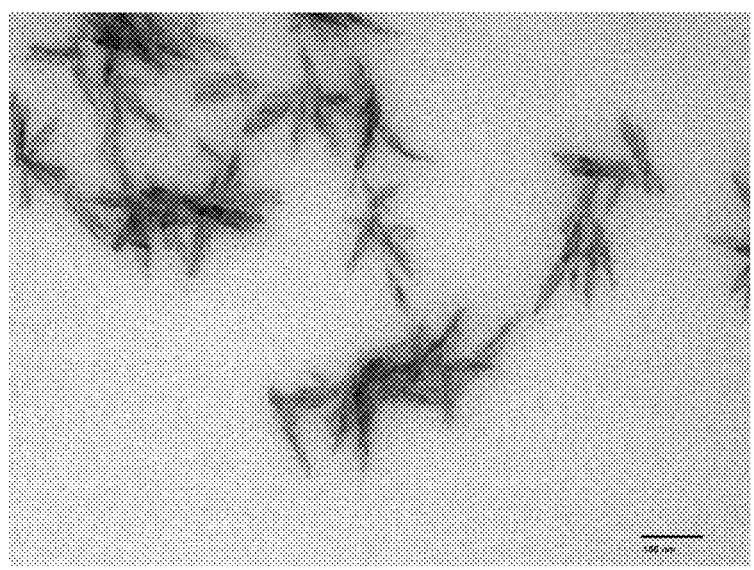
FIG. 9. Shows TEM images of valsartan particles obtained by the electro-nebulizer, after dissolving the polymer in cold deionized water in example 4.

In order to observe the morphology of the drug inside the particles inside the HPMC microparticle, the polymer was dissolved in cold deionized water and the morphology of the drug is observed by TEM. The drug exhibits a submicron size needle shape, which is shown in FIG. 9.

The obtained encapsulated Valsartan particles are being used for the finished product manufacturing by usage of conventional pharmaceutical techniques.

Example 5

HPMC-abiraterone acetate microparticles (percentage of API in the particle is of 63% by weight)

In this example, the encapsulation of abiraterone acetate in HPMC is described, using the electro-nebulizer, with a percentage of API in the particle of 63% by weight.

Emulsion Preparation:

An oil in water (O/W) emulsion was used, with a ratio organic phase: aqueous phase of 30:70. In a first step, the aqueous phase of the emulsion is prepared. The polymer is dissolved in cold deionized water with a concentration of 20 mg/ml. 10 mg/mL of TEGO (TEGO® SML sorbitan fatty acid ester) is dissolved in this mixture. The organic phase of the emulsion consisted of 120 mg/ml of abiraterone acetate in ethanol 85%. The organic phase is slowly added over the aqueous phase and stirred in the ultraturrax for 5 min at 17,000 rpm, followed by 1 min of ultrasounds to achieve a homogeneous size distribution of the micelles of the emulsion. During the stirring, the emulsion is maintained in a cold bath to prevent emulsion temperature from rising.

Electro-Nebulizer Process:

Once the emulsion has been obtained, it is immediately used to generate microparticles by the electro-nebulizer. The emulsion is introduced in the drying chamber by means of the injection equipment at a flowrate of 10 mL/min. This injection equipment has an electro-nebulizer to generate an aerosol of the emulsion and, thus, guarantees an adequate evaporation of the solvent. This electro-nebulizer operates with a compressed air flowrate of 10 L/min and a voltage of 10 kV. The drops of the aerosol are dried by means of 85 $m^3/h$ of process air, in co-current mode, and at room temperature. The dried microparticles are collected on a cyclone.

Finished Product:

The tablet was formulated as one swallowable dosage form which is bio-equivalent to two 500 mg tablets of Zytiga® reference product or four 250 mg tablets of Zytiga®. The smaller strengths might be produced by using the proportional formulation for abiraterone acetate tablets made by the technology described in the present invention.

The invention claimed is:

1. A method to prepare sub-micron particles between 1 and 800 nm of at least one active pharmaceutical ingredient or pharmaceutical acceptable salt thereof encapsulated into microparticles between 1 and 100 μm comprising excipients, the method practiced in a facility comprising:

an injection unit, which is an electronebulizer, comprising at least:

one inlet for an emulsion;

one inlet for injection gas; and one outlet for droplets through which sprayed droplets of emulsion are released, a drying unit, which is arranged after the injection unit, and a collection unit, arranged after the drying unit;

the method comprises the following steps:

a) preparing of an emulsion comprising:

at least one active pharmaceutical ingredient or pharmaceutically acceptable salt thereof to be encapsulated, one or more excipients;

at least two non-miscible or partially miscible solvents or two miscible solvents that by solubilizing the API or the excipients become non-miscible or partially miscible solvents, b) forming droplets of nano-embedded microparticles in only one step by the electronebulizer from the emulsion obtained in stage (a) in the presence of an injection gas flow that creates the droplets and applying a voltage of between 0.1 kV and 500 kV at the outlet of the injection unit, c) drying the droplets obtained in stage (b) in the drying unit at a controlled room temperature to obtain the microparticles; and d) collecting the microparticles obtained in stage (c) by means of the collection unit.

2. The method according to claim 1 wherein the excipient used in stage a) further comprising a surfactant to stabilize the emulsion.

3. The method according to claim 1 wherein the solvents used in step a) are selected from the list consisting of: water, alcohol, toluene, ethyl acetate, methylene chloride, chloroform, dimethyl sulfoxide, dimethyl formamide, tetrahydrofuran, deep eutectic solvents, natural deep eutectic solvents and combinations thereof.

* * * * *